US010299750B2

United States Patent
Funabasama et al.

(10) Patent No.: US 10,299,750 B2
(45) Date of Patent: May 28, 2019

(54) MEDICAL IMAGE PROCESSING APPARATUS AND X-RAY CT APPARATUS

(71) Applicant: Toshiba Medical Systems Corporation, Otawara-shi (JP)

(72) Inventors: Shintaro Funabasama, Utsunomiya (JP); Yasuko Fujisawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/662,523

(22) Filed: Jul. 28, 2017

(65) Prior Publication Data
US 2018/0035964 A1 Feb. 8, 2018

(30) Foreign Application Priority Data

Aug. 5, 2016 (JP) ................................. 2016-154733
Jul. 25, 2017 (JP) ................................. 2017-143941

(51) Int. Cl.
*A61B 6/00* (2006.01)
*G06T 7/00* (2017.01)
(Continued)

(52) U.S. Cl.
CPC .............. *A61B 6/505* (2013.01); *A61B 6/032* (2013.01); *A61B 6/463* (2013.01); *A61B 6/465* (2013.01);
(Continued)

(58) Field of Classification Search
CPC ..... A61B 6/505; A61B 5/4514; A61B 5/4528; A61B 6/4035; A61B 6/484; A61B 6/5217;
(Continued)

(56) References Cited

U.S. PATENT DOCUMENTS 5,692,117 A * 11/1997 Berend ................. G06T 11/001
345/475
5,864,146 A * 1/1999 Karellas .................... A61B 6/06
250/581
(Continued)

FOREIGN PATENT DOCUMENTS

JP 2010-253243 11/2010
JP 4934786 5/2012
(Continued)

*Primary Examiner* — Aklilu K Woldemariam
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry detects three or more bones and a joint space region from three-dimensional medical image data captured for images of a joint formed between the three or more bones, the joint space region corresponding to a joint space of the joint. The processing circuitry divides the joint space region into a plurality of small regions corresponding to different pairs of opposed bones of the three or more bones. The processing circuitry obtains information on each of the small regions based on the small regions into which the joint space region has been divided that correspond to the different pairs of bones. The processing circuitry outputs the obtained information.

14 Claims, 9 Drawing Sheets

(51) Int. Cl.
*A61B 6/03* (2006.01)
*G06T 5/50* (2006.01)

(52) U.S. Cl.
CPC .............. *A61B 6/48* (2013.01); *A61B 6/486* (2013.01); *A61B 6/5217* (2013.01); *A61B 6/5235* (2013.01); *G06T 5/50* (2013.01); *G06T 7/0012* (2013.01); *A61B 6/5205* (2013.01); *G06T 2200/04* (2013.01); *G06T 2207/10081* (2013.01); *G06T 2207/30008* (2013.01)

(58) Field of Classification Search
CPC ........ A61B 5/05; A61B 5/055; A61B 5/4509; A61B 5/4533; A61B 6/032; A61B 6/5211; A61B 6/548; A61B 17/320068; A61B 18/12; A61B 18/1206; A61B 18/1482; A61B 18/20; A61B 1/00009; A61B 2017/00477; A61B 2017/00973; A61B 34/25; A61B 34/30; A61B 34/37; A61B 90/361; A61B 5/1075; A61B 6/00; A61B 6/463; A61B 6/48; A61B 6/5235; G06T 2207/30008; G06T 2207/10116; G06T 7/0012; G06T 7/12; G06T 7/62; G06T 7/0083; G06T 7/602; G06T 11/008; G06T 13/80; G06T 19/00; G06T 2210/41; G06T 7/20; G06T 13/40; G06T 2210/16; G06T 19/20; G06T 2219/2021; G06T 17/205; G06T 2207/10016; G06T 2207/30204; G06T 2213/04; G06T 2219/20; G06T 7/251; G06T 2207/20096; G06T 5/50; G06T 7/60; G06T 2200/04; G06T 2207/10081; G06T 2207/10072; G06T 2207/30048; G06T 2207/30101; G06T 7/11; G05B 19/0426; G06F 19/00; G06F 9/451; G16H 50/50; G06K 2009/3225; G06K 2209/055; G06K 9/00369; G06K 9/3216; G06K 9/4638; G06K 9/6224; Y10S 707/09
USPC ....... 382/128, 129, 130, 131, 199, 257, 154, 382/288; 715/762, 810, 747; 600/407, 600/410; 345/440, 473
See application file for complete search history.

(56) References Cited

U.S. PATENT DOCUMENTS

| | | | |
|---|---|---|---|
| 6,711,282 B1 * | 3/2004 | Liu | G01N 23/04 378/54 |
| 6,711,432 B1 * | 3/2004 | Krause | A61B 17/15 128/922 |
| 7,236,817 B2 * | 6/2007 | Papas | A61B 5/055 600/427 |
| 7,664,297 B2 | 2/2010 | Harada et al. | |
| 8,696,603 B2 | 4/2014 | Takahashi et al. | |
| 2002/0070365 A1 * | 6/2002 | Karellas | A61B 6/06 250/581 |
| 2003/0023156 A1 * | 1/2003 | Pappas | A61B 5/055 600/407 |
| 2004/0021660 A1 * | 2/2004 | Ng-Thow-Hing | G06K 9/00369 345/419 |
| 2004/0068187 A1 * | 4/2004 | Krause | A61B 17/15 600/443 |
| 2004/0136583 A1 * | 7/2004 | Harada | A61B 6/505 382/131 |
| 2007/0031015 A1 * | 2/2007 | Chen | G06T 7/0012 382/128 |
| 2009/0136103 A1 * | 5/2009 | Sonka | G06K 9/4638 382/128 |
| 2010/0145231 A1 * | 6/2010 | Takahashi | A61B 5/1075 600/587 |
| 2010/0152724 A1 * | 6/2010 | Marion | A61B 5/01 606/33 |
| 2012/0154277 A1 * | 6/2012 | Bar-Zeev | G02B 27/017 345/158 |
| 2013/0272594 A1 * | 10/2013 | Zelzer | G06T 3/0043 382/131 |
| 2015/0150529 A1 * | 6/2015 | Hoshino | A61B 6/484 378/36 |
| 2016/0022349 A1 * | 1/2016 | Woloszko | A61B 18/14 606/34 |
| 2017/0032055 A1 * | 2/2017 | Eisemann | G06F 17/10 |
| 2017/0032579 A1 * | 2/2017 | Eisemann | G06T 13/40 |

FOREIGN PATENT DOCUMENTS

| | | |
|---|---|---|
| JP | 2015-104441 | 6/2015 |
| WO | WO 02/087444 A1 | 11/2002 |

* cited by examiner ately evaluate joint spaces.

MEDICAL IMAGE PROCESSING APPARATUS AND X-RAY CT APPARATUS

CROSS-REFERENCE TO RELATED APPLICATIONS

This application is based upon and claims the benefit of priority from Japanese Patent Application No. 2016-154733, filed on Aug. 5, 2016; and Japanese Patent Application No. 2017-143941, filed on Jul. 25, 2017, the entire contents of all of which are incorporated herein by reference.

FIELD

Embodiments described herein relate generally to a medical image processing apparatus and an X-ray computed tomography (CT) apparatus.

BACKGROUND

Conventionally, image analysis on medical image data involves quantitative evaluation of a space (also called "joint space") between bones that form a joint therebetween. For example, the distance between two points designated by an operator in two-dimensional projected image data captured by plain radiography is measured as the width of a joint space. Also for example, the area of a region designated by an operator in projected image data is measured as the size of a joint space.

Various techniques have been proposed for enabling automatic measurement of a joint space. For example, based on information on anatomical features of a joint to be evaluated, a region corresponding to the joint is extracted from projected image data. Thereafter, the maximum and minimum values of the width of a joint space and the area of a corresponding region are automatically measured. For such a technique, dedicated computer programs for different kinds of joint, such as one for knee joints and one for hip joints, are developed.

DETAILED DESCRIPTION

Embodiments described herein are aimed at providing a medical image processing apparatus and an X-ray CT apparatus that enable accurate and simplified quantitative evaluation on joint spaces.

A medical image processing apparatus according to each embodiment includes processing circuitry. From three-dimensional medical image data captured for images of a joint formed between three or more bones, the processing circuitry detects the three or more bones and a joint space region that corresponds to a joint space of the joint. Based on the detected three or more bones and the shape of the joint space region, the processing circuitry divides the joint space region into a plurality of small regions corresponding to different pairs of opposed bones of the three or more bones. The processing circuitry then obtains information on each of the small regions based on the small regions into which the joint space region has been divided that correspond to the different pairs of bones, and outputs the obtained information.

The following describes embodiments of a medical image processing apparatus and an X-ray CT apparatus. Each of the following embodiments cites, as examples, an X-ray CT apparatus that captures X-ray CT image data of a subject. However, the embodiments are not limited to being applied to an X-ray CT apparatus and are broadly applicable to medical image processing apparatuses (computers) capable of processing medical images. Exemplary medical image processing apparatuses applicable thereto include not only an X-ray CT apparatus but also an X-ray diagnosis apparatus, a magnetic resonance imaging (MRI) apparatus, a single photon emission computed tomography (SPECT) apparatus, a positron emission computed tomography (PET), a SPECT-CT apparatus obtained by integrating a SPECT apparatus and an X-ray CT apparatus, a PET-CT apparatus obtained by integrating a PET apparatus and an X-ray CT apparatus, and a medical image processing apparatus composed as a set of two or more apparatuses such as those listed above.

First Embodiment

Figure 1:
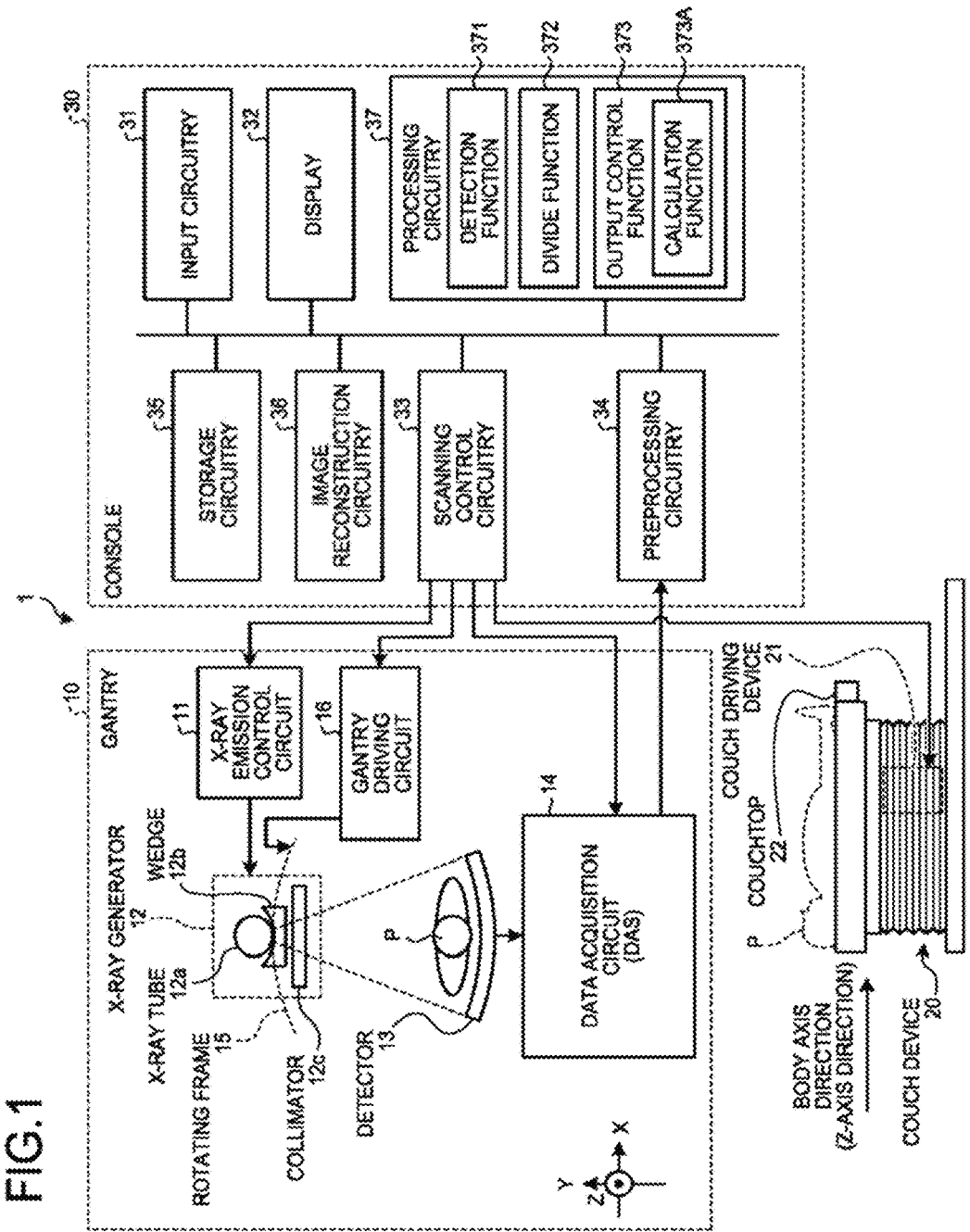
FIG. 1 is a diagram illustrating an example of the configuration of an X-ray CT apparatus according to a first embodiment.

FIG. 1 is a diagram illustrating an example of the configuration of an X-ray CT apparatus 1 according to a first embodiment. As illustrated in FIG. 1, the X-ray CT apparatus 1 according to the first embodiment includes a gantry 10, a couch device 20, and a console 30.

The gantry 10 is a device configured to emit X-rays to a subject P (patient), detect X-rays having passed through the subject P, and output thus obtained data to the console 30, and includes an X-ray emission control circuit 11, an X-ray generator 12, a detector 13, a data acquisition circuit (data acquisition system (DAS)) 14, a rotating frame 15, and a gantry driving circuit 16.

The rotating frame 15 is an annular frame supporting the X-ray generator 12 and the detector 13 so as to have them opposed to each other across the subject P, and rotates at high speed on a circular orbit about the subject P under the control of the gantry driving circuit 16 to be described later.

The X-ray emission control circuit 11 is a device that, as a high-voltage generator, supplies a high voltage to an X-ray tube 12a, and the X-ray tube 12a generates X-rays using the high voltage supplied from the X-ray emission control circuit 11. The X-ray emission control circuit 11 adjusts a tube voltage and a tube current that are supplied to the X-ray tube 12a under the control of scanning control circuitry 33 to be described later, thereby adjusting the X-ray dose to which the subject P is exposed.

The X-ray emission control circuit 11 switches wedges 12b from one to another. The X-ray emission control circuit 11 adjusts the X-ray radiation field (the fan angle and the cone angle) by adjusting the size of the aperture of a collimator 12c. This embodiment may be applied to a case in which an operator manually switches a plurality of kinds of wedges.

The X-ray generator 12 is a device configured to generate X-rays and emit the generated X-rays to the subject P, and includes the X-ray tube 12a, any one of the wedges 12b, and the collimator 12c.

The X-ray tube 12a is a vacuum tube for emitting an X-ray beam to the subject P using a high voltage supplied thereto from the high-voltage generation unit (not illustrated), and emits the X-ray beam to the subject P while the rotating frame 15 rotates. The X-ray tube 12a generates an X-ray beam radiating in a manner defined by a fan angle and a cone angle. For example, under the control of the X-ray emission control circuit 11, the X-ray tube 12a can continuously expose the subject P to X-rays at the entire circumference of the subject P for the full reconstruction purpose or can continuously expose the subject P to X-rays in an exposure range (180 degrees+fan angle) enabling half reconstruction for the half reconstruction purpose. The X-ray tube 12a can also intermittently expose the subject P to X-rays (pulse X-rays) at preset positions (tube bulb positions) under the control of the X-ray emission control circuit 11. The X-ray emission control circuit 11 can also modulate the intensity of X-rays to be emitted from the X-ray tube 12a. The X-ray emission control circuit 11 increases the intensity of X-rays to be emitted from the X-ray tube 12a at a specified tube bulb position and decreases the intensity of X-rays to be emitted from the X-ray tube 12a in a range other than the specified tube bulb position, for example.

Each of the wedges 12b is an X-ray filter for adjusting the X-ray dose of X-rays to be emitted from the X-ray tube 12a. Specifically, the wedge 12b is a filter that transmits and attenuates X-rays emitted from the X-ray tube 12a so that the X-rays emitted from the X-ray tube 12a to the subject P can be distributed in a previously determined manner. The wedge 12b is, for example, a filter obtained by processing aluminum into a form having a predetermined target angle and a predetermined thickness. The wedge 12b is also called a wedge filter or a bow-tie filter.

The collimator 12c is a slit for narrowing an X-ray radiation field having an X-ray dose adjusted by the wedge 12b under the control of the X-ray emission control circuit 11.

The gantry driving circuit 16 drives the rotating frame 15 into rotation, thereby causing the X-ray generator 12 and the detector 13 to circle around the subject P on a circular orbit.

Being a two-dimensional array detector (flat panel detector) for detecting X-rays that have passed through the subject P, the detector 13 has a plurality of detection element rows arranged side by side in the Z-axis direction, the detection element rows each having X-ray detection elements, corresponding to a plurality of channels, arranged therein. Specifically, the detector 13 in the first embodiment includes the X-ray detection elements arrayed in multiple rows, such as 320 rows, arranged side by side along the Z-axis direction, and is capable of detecting X-rays that have passed through the subject P over a wide range, such as a range including the lungs and the heart of the subject P. The Z-axis direction herein corresponds to a direction along the central axis of rotation of the rotating frame 15 with the gantry 10 not tilted.

The data acquisition circuit 14 is a DAS and acquires projection data from detection data on X-rays detected by the detector 13. For example, the data acquisition circuit 14 generates the projection data by performing processing such as amplification, analog-to-digital (A/D) conversion, and sensitivity correction between channels on data on the X-ray intensity distribution detected by the detector 13, and transmits the generated projection data to the console 30 to be described later. For example, when, the X-ray tube 12a continuously emits X-rays with the rotating frame 15 rotating, the data acquisition circuit 14 acquires a group of projection data corresponding to the entire circumference (360 degrees). The data acquisition circuit 14 sends the acquired projection data to the console 30, to be described later, while associating the data with tube bulb positions. The tube bulb positions are information indicating projection directions of projection data. Instead, preprocessing circuitry 34 to be described later may perform the sensitivity correction processing between the channels.

The couch device 20 is a device on which the subject P is placed, and includes a couch driving device 21 and a couchtop 22, as illustrated in FIG. 1. The couch driving device 21 moves the couchtop 22 in the Z-axis direction to move the subject P into the rotating frame 15. The couchtop 22 is a plate on which the subject P is placed.

The gantry 10 executes, for example, a helical scan in which it scans the subject P in a spiral manner by rotating the rotating frame 15 while moving the couchtop 22. Alternatively, the gantry 10 executes a conventional scan in which it scans the subject P on a circular orbit by, after moving the couchtop 22, rotating the rotating frame 15 with the subject P kept in a fixed position. Alternatively, the gantry 10 executes a step-and-shoot process in which it performs conventional scans for a plurality of scan areas by moving the position of the couchtop 22 at certain intervals.

The console 30 is a device configured to receive an operation on the X-ray CT apparatus 1 from the operator and reconstruct X-ray CT image data using projection data acquired by the gantry 10. The console 30 includes, as illustrated in FIG. 1, input circuitry 31, a display 32, the scanning control circuitry 33, the preprocessing circuitry 34, storage circuitry 35, image reconstruction circuitry 36, and processing circuitry 37. The input circuitry 31, the display 32, the scanning control circuitry 33, the preprocessing circuitry 34, the storage circuitry 35, the image reconstruction circuitry 36, and the processing circuitry 37 are connected together so as to be communicable with each other.

The input circuitry 31 includes a mouse, a keyboard, a trackball, a switch, a button, or a joystick that is used by the operator of the X-ray CT apparatus 1 to input various instructions and various settings, and transmits information about instructions or settings received from the operator to the processing circuitry 37. The input circuitry 31 receives, for example, radiographic conditions for X-ray CT image data, reconstruction conditions for reconstruction of X-ray CT image data, and conditions for image processing on X-ray CT image data, from the operator. The input circuitry 31 also receives an operation for selecting an examination to be performed on the subject P. The input circuitry 31 also receives a specification operation for specifying a site on an image.

Being a monitor that the operator checks, the display 32 is operable to, under the control of the processing circuitry 37, display, to the operator, image data generated from X-ray CT image data, and display a graphical user interface (GUI) for receiving various instructions, various settings, and the like from the operator through the input circuitry 31. The display 32 also displays screens such as a screen for planning a scanning plan and a screen regarding an ongoing scan.

Under the control of the processing circuitry 37, the scanning control circuitry 33 controls processing of projection data acquisition in the gantry 10 by controlling operation of the X-ray emission control circuit 11, the gantry driving circuit 16, the data acquisition circuit 14, and the couch driving device 21. Specifically, the scanning control circuitry 33 controls processing of projection data acquisition both in positioning imaging for acquiring positioning images (scanogram images) and in main imaging (main scanning) for acquiring images that are used for diagnosis.

The scanning control circuitry 33 captures two-dimensional scanogram images by continuously capturing images while moving the couchtop 22 at a constant speed with the X-ray tube 12a kept stationary at the zero-degree position (a position facing the front side of the subject). Alternatively, the scanning control circuitry 33 captures two-dimensional scanogram images by, while intermittently moving the couchtop 22 with the X-ray tube 12a fixed at the zero-degree position, intermittently repeatedly capturing images in synchronization with the move of the couchtop. The scanning control circuitry 33 herein can capture positioning images not only from the position facing the front side of the subject P but also from another position facing any side (for example, a position facing a lateral side) thereof.

The scanning control circuitry 33 acquires projection data corresponding to the entire circumference of a subject, thereby capturing three-dimensional X-ray CT image data (volume data). For example, the scanning control circuitry 33 acquires projection data corresponding to the entire circumference of the subject P by helical scanning or non-helical scanning. The scanning control circuitry 33 can also capture three-dimensional scanogram images by acquiring projection data corresponding to the entire circumference at a lower dose than in main imaging.

Furthermore, the scanning control circuitry 33 can perform dynamic volume scanning (also called "dynamic scanning") in which it can continuously capture volume data for a certain period of time to capture a plurality of pieces of volume data arranged in a time sequence. For example, the scanning control circuitry 33 can, by continuously acquiring projection data corresponding to the entire circumference with the subject P moving a certain joint, capture a plurality of pieces of volume data reconstructed at a certain frame rate (volume rate). Time-sequential volume data captured through dynamic scanning is called four-dimensional X-ray CT image data, or 4DCT image data.

The preprocessing circuitry 34 generates corrected projection data by performing logarithmic conversion processing and correction processing, such as offset correction, sensitivity correction, and beam hardening correction, on projection data generated by the data acquisition circuit 14. Specifically, the preprocessing circuitry 34 generates corrected projection data for projection data of positioning images and projection data acquired in main imaging that have been generated by the data acquisition circuit 14, and stores the corrected projection data in the storage circuitry 35.

The storage circuitry 35 stores therein projection data generated by the preprocessing circuitry 34. Specifically, the storage circuitry 35 stores therein projection data of the positioning images and projection data for diagnosis acquired in main scanning that have been generated by the preprocessing circuitry 34. The storage circuitry 35 also stores therein data such as X-ray CT image data generated by the image reconstruction circuitry 36 to be described later. The storage circuitry 35 also stores therein results of processing performed by the processing circuitry 37 to be described later.

The image reconstruction circuitry 36 reconstructs X-ray CT image data using projection data stored in the storage circuitry 35. Specifically, the image reconstruction circuitry 36 reconstructs X-ray CT image data from projection data of the positioning images and projection data of images that are used for diagnosis, respectively. There are various methods for reconstruction, examples of which include an inverse projection process. Furthermore, examples of the inverse projection process include an inverse projection process based on a filtered back projection (FBP) method. Alternatively, the image reconstruction circuitry 36 can reconstruct X-ray CT image data using a successive approximation method. The image reconstruction circuitry 36 performs various kinds of image processing on X-ray CT image data to generate image data. The image reconstruction circuitry 36 then stores the reconstructed X-ray CT image data and the image data generated by the various kinds of image processing in the storage circuitry 35. The image reconstruction circuitry 36 is an example of an image reconstructor.

Furthermore, the image reconstruction circuitry 36 reconstructs time-sequential three-dimensional medical image data (4DCT image data) captured through dynamic scanning. For example, the image reconstruction circuitry 36 reconstructs, at a certain frame rate, projection data that corresponds to the entire circumference and that has been continuously acquired for a certain period of time, thus reconstructing a plurality of pieces of volume data arranged in a time sequence. Thus, volume data (4DCT image data) can be reconstructed that corresponds to consecutive multiple frames (time phases) representing a manner in which a certain joint is moved.

The processing circuitry 37 controls the entire X-ray CT apparatus 1 by controlling operation of the gantry 10, the couch device 20, and the console 30. Specifically, the processing circuitry 37 controls the scanning control circuitry 33 to control CT scans that the gantry 10 executes. The processing circuitry 37 also controls the image reconstruction circuitry 36 to control image reconstruction processing and image generation processing in the console 30. Furthermore, the processing circuitry 37 performs control so that various pieces of image data stored in the storage circuitry 35 can be displayed on the display 32.

Additionally, the output control function 373 executes a detection function 371, a divide function 372, and an output control function 373 as illustrated in FIG. 1. In this case, for example, processing functions to be performed by the detection function 371, the divide function 372, and the output control function 373 provided as components of the processing circuitry 37 illustrated in FIG. 1 are stored as computer programs executable by a computer in the storage circuitry 35. The processing circuitry 37 is a processor that loads and executes each of the computer programs stored in the storage circuitry 35 to implement the function corresponding to the loaded and executed computer program. In other words, when having loaded each of the computer programs, the processing circuitry 37 is equipped with a corresponding one of the functions illustrated in the processing circuitry 37 in FIG. 1. The respective processing functions to be executed by the detection function 371, the divide function 372, and the output control function 373 are to be described later.

While this embodiment, is described on the assumption that the processing functions are implemented in the processing circuitry 37 composed of a single processor, the processing functions may be implemented in a manner such that, in the processing circuitry 37 composed of a combination of a plurality of independent processors, the processors execute the respective computer programs.

The term "processor" as used in the above description means, for example, a central processing unit (CPU), a graphics processing unit (GPU), or a circuit such as an application specific integrated circuit (ASIC), a programmable logic device (for example, a simple programmable logic device (SPLD), a complex programmable logic device (CPLD), or a field programmable gate array (FPGA)). Each processor loads and executes a computer program stored in the storage circuitry 35 to implement a function. Instead of being stored in the storage circuitry 35, each computer program may be directly embedded in a circuit in a processor. In such a case, the processor leads and executes the computer program embedded in the circuit to implement a function. Being not limited to a processor built as a single circuit, each of the processors in this embodiment may be built as a processor composed of a combination of a plurality of independent circuits so as to implement functions corresponding to the circuits. Further alternatively, two or more components in each drawing may be integrated into a single processor for implementation of functions thereof.

The configuration of the X-ray CT apparatus 1 according to the first embodiment has been described. Being thus configured, the X-ray CT apparatus 1 according to the first embodiment executes the processing functions as follows for enabling accurate and simplified quantitative evaluation on a joint space.

While the following description illustrates a case in which the X-ray CT apparatus 1 according to this embodiment performs processing on 4DCT image data, the embodiment is not limited thereto. For example, the X-ray CT apparatus 1 may perform processing on three-dimensional X-ray CT image data for a still image captured at a certain point in time.

From three-dimensional medical image data captured for images of a joint formed between three or more bones, the detection function 371 detects a joint space region that corresponds to a joint space of the joint. For example, from three-dimensional medical image data captured for images of a joint formed between three or more bones, the detection function 371 detects, as a joint space region, a region between two opposed ones of these three or more bones that includes perpendiculars of a plane equally distant from the two opposed bones with the opposite ends of each of the perpendiculars intersecting the two respective bones. The detection function 371 detects a joint space region with respect to each frame of three-dimensional medical image data captured in a time sequence. The detection function 371 is an example of a detector.

Figure 2:
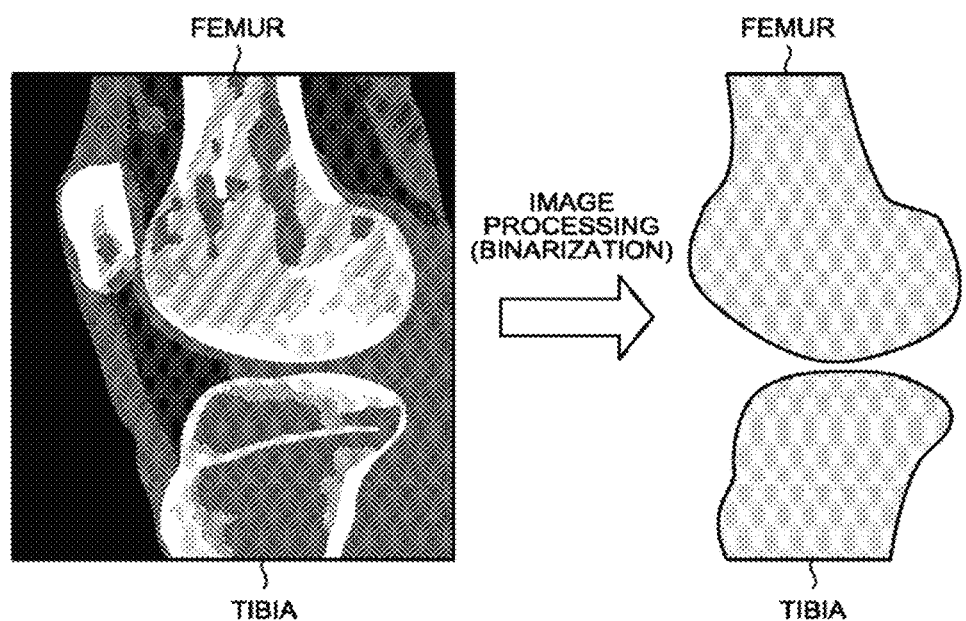
FIG. 2 is an illustration explaining processing that a detection function according to the first embodiment performs.
Figure 3:
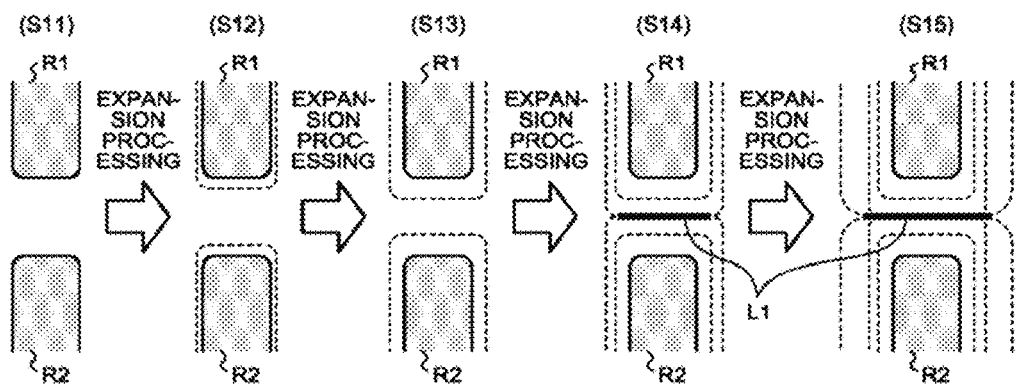
FIG. 3 is an illustration for explaining processing that the detection function according to the first embodiment performs.
Figure 4:
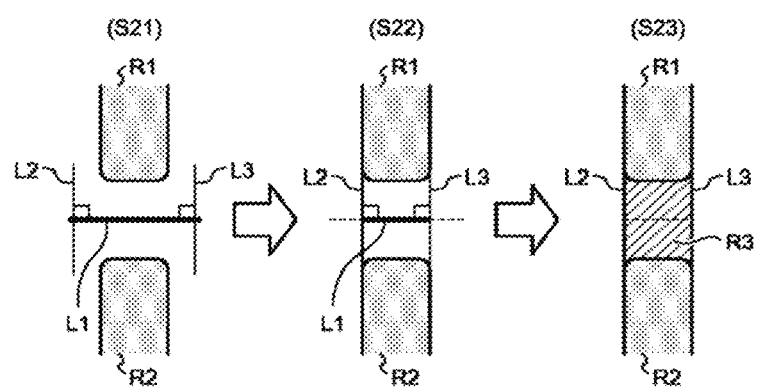
FIG. 4 is an illustration for explaining processing that the detection function according to the first embodiment performs.
Figure 5:
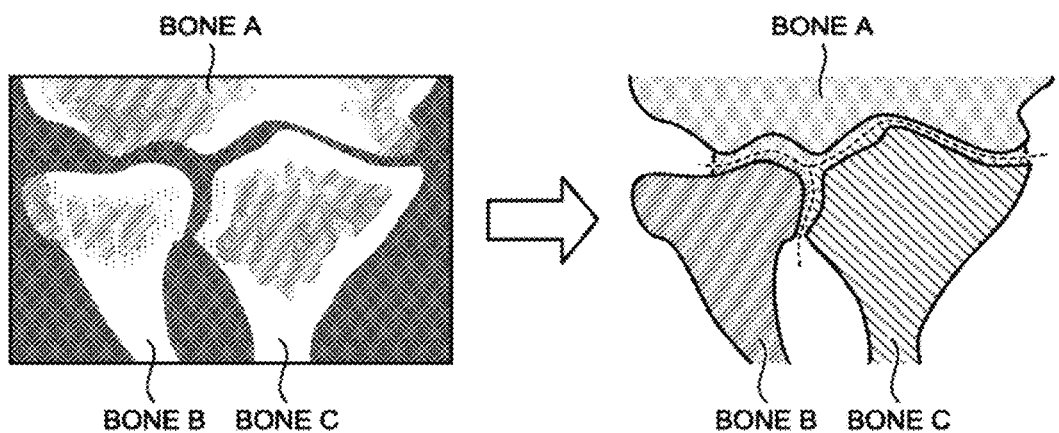
FIG. 5 is an illustration for explaining processing that the detection function according to the first embodiment performs.

FIG. 2 to FIG. 5 are illustrations for explaining processing that the detection function 371 according to the first embodiment performs. FIG. 2 illustrates processing (image processing) for detecting the regions of bones. FIG. 3 illustrates processing for detecting a plane equally distant from these bones. FIG. 4 illustrates processing for detecting a region that includes perpendiculars of the plane with the opposite ends of each of the perpendiculars intersecting these bones. FIG. 5 illustrates a case in which joint space regions between three bones is detected. While FIG. 2 to FIG. 5 explain a case in which the corresponding processing is executed on X-ray CT image data in a certain frame, the same processing is similarly executed on the other frames, whereby the processing is performed on 4DCT image data. In addition, FIG. 2 to FIG. 5 illustrate the processing, for the convenience of illustration, as if it is performed on a flat image, image data actually subject to the processing is three-dimensional X-ray CT image data. In other words, FIG. 2 to FIG. 5 explain the corresponding processing assuming that it is processing on a certain section in X-ray CT image data.

As illustrated in FIG. 2, the detection function 371 detects regions of a plurality of bones by performing image processing such as binarization on three-dimensional medical image data. The illustration in the left side of FIG. 2 is a sectional image in X-ray CT image data in which images of a knee joint have been captured. The sectional image has a femur (in the upper part of the illustration) and a tibia (in the lower part of the illustration) visualized therein. For example, the detection function 371 binarizes the X-ray CT image data using a threshold determined in accordance with a CT value for a bone. The detection function 371 then performs image processing on the X-ray CT image data for eliminating noise therefrom. The noise elimination is carried out, for example, by repeatedly performing expansion processing in which a region of a bone detected through the binarization is expanded by one pixel (voxel) at a time and contraction processing in which the region is contracted by one pixel at a time. The detection function 371 detects regions corresponding to the femur and the tibia (in the right part of FIG. 2) from the X-ray CT image data (in the left part of FIG. 2).

Subsequently, as illustrated in FIG. 3, the detection function 371 performs expansion processing on the detected regions of the respective bones, thereby detecting a plane equally distant from two opposed ones of the bones. FIG. 3 explains a case in which a plane between regions R1 and R2 detected through the binarization. For example, the detection function 371 performs expansion processing in which the detected regions R1 and R2 are expanded outward by one pixel with respect to each of the outermost pixels thereof. Specifically, before the expansion processing is performed, the regions R1 and R2 are located a certain distance from each other (S11). When the detection function 371 performs the one-pixel outward expansion processing, each of the regions R1 and R2 are expanded outward by one pixel with respect to each of the outermost pixels thereof (as indicated by the broken lines at S12). Subsequently, the detection function 371 further performs the one-pixel outward expansion processing, and each of the regions R1 and R2 are further expanded outward by one pixel with respect to each of the outermost pixels thereof (as indicated by the broken lines at S13). When the detection function 371 thus repeats the expansion processing, the regions R1 and R2 make contact with each other after the processing is repeated a certain number of times, so that the line L1 is formed (S14). After the line L1 is formed, the detection function 371 is stopped from performing the expansion processing on pixels on the line L1. That is, the detection function 371 repeatedly performs the expansion processing a previously determined number of times under the rule that the expansion processing is stopped from being further performed on pixels on a position at which the regions have made contact with each other. The number of times the expansion processing repeatedly performed is previously determined by the operator based on, for example, normal values of the width (distance) of a joint space. The detection function 371 thus detects the position of the line L1 equally distant from the regions R1 and R2 by repeatedly performing the expansion processing a previously determined number of times (S15). The line L1 detected in a sectional image is detected as a plane in three-dimensional X-ray CT image data.

As illustrated in FIG. 4, the detection function 371 then detects, as a joint space region, a region that includes perpendiculars of the detected plane (presented as the "line" in the illustration) with the opposite ends of each of the perpendiculars intersecting different bones. For example, the detection function 371 constructs perpendiculars L2 and L3 of the line L1 detected in FIG. 3, having previously determined lengths, through the respective opposite ends of the line L1 (S21). The lengths of the respective perpendiculars L2 and L3 are previously determined by the operator based on, for example, normal values of the width (distance) of a joint space. The detection function 371 moves the perpendiculars L2 and L3 toward the center of the line L1 to search for a position at which the opposite ends of each of the perpendiculars L2 and L3 intersect different bones. In the example of FIG. 4, the perpendicular L2 moves rightward for the searching and the perpendicular L3 moves leftward for the searching. The searching is continued until the opposite ends of each of the perpendiculars L2 and L3 intersect the bones (S22). In the example in FIG. 4, the upper end of the perpendicular L1 intersects the region R1 and the lower end thereof intersects the region R2. The upper end of the perpendicular L3 intersects the region R1 and the lower end thereof intersects the region R2. The detection function 371 then detects, as a joint space region, the region R3 surrounded by the region R1, the region R2, the perpendicular L2, and the perpendicular L3 (S23). The perpendiculars L2 and L3 constructed in the sectional image are constructed as "planes" in the three-dimensional X-ray CT image data. That is, the detection function 371 constructs planes perpendicular of the line L1, which is a plane, and the perpendicular planes thus constructed are moved toward the center to search for a region surrounded by the perpendicular planes and the bones.

As illustrated in FIG. 5, also in the case of a joint formed between three bones, the detection function 371 performs the same processing as those illustrated in FIG. 2 to FIG. 4 to search for a joint space region. For example, the detection function 371 detects the respective regions of the bone A, the bone B, and the bone C by performing image processing including binarization on X-ray CT image data (the illustration in the left side of FIG. 5) captured for images of a joint formed between the bone A, the bone B, and the bone C. The detection function 371 then detects lines (planes in three-dimensional data) equally distant from any two bones of the bone A, the bone B, and the bone C by performing expansion processing on the respective regions of the bone A, the bone B, and the bone C. The detection function 371 then detects a joint space region between the bone A, the bone B, and the bone C by searching for a region surrounded by perpendiculars (planes in the case of three-dimensional data) constructed through the ends of the line equally distant from any two bones each of the lines (the right illustration in FIG. 5).

The detection function 371 thus detects, as a joint space region, each region including a plane equally distant from two opposed bones among a plurality of bones, the region including perpendiculars of the plane with the opposite ends of each of the perpendiculars intersecting the two different bones. In other words, from three-dimensional medical image data captured for images of a joint formed between three or more bones, the detection function 371 detects the three or more bones and a joint space region that corresponds to a joint space of the joint. The above description of the detection function 371 is merely an example and is not limiting. For example, processing for eliminating noise described in FIG. 2 is not limited to repeatedly performing expansion processing and contraction processing and may be performed by smoothing processing on an image In this embodiment, the term "opposed bones" means, for example, the bone A and the bone B, which are a pair of bones adjacent to each other across a joint space as illustrated in FIG. 5, and does not necessarily mean bones that are making contact with each other. That is, the term "opposed bone" means bones that function as a pair of bones at positions across a joint space regardless of whether these bones make contact with each other.

The divide function 372 divides a joint space region into regions corresponding to the different pairs of opposed bones. For example, the divide function 372 divides a joint space region while taking, as each of the pairs of bones, two opposed bones that are intersected by the opposite ends of any perpendicular of a line equally distant from these bones. The divide function 372 divides a joint space region with respect to each frame in three-dimensional medical image data captured in a time sequence. The divide function 372 is an example of a divide unit.

Figure 6:
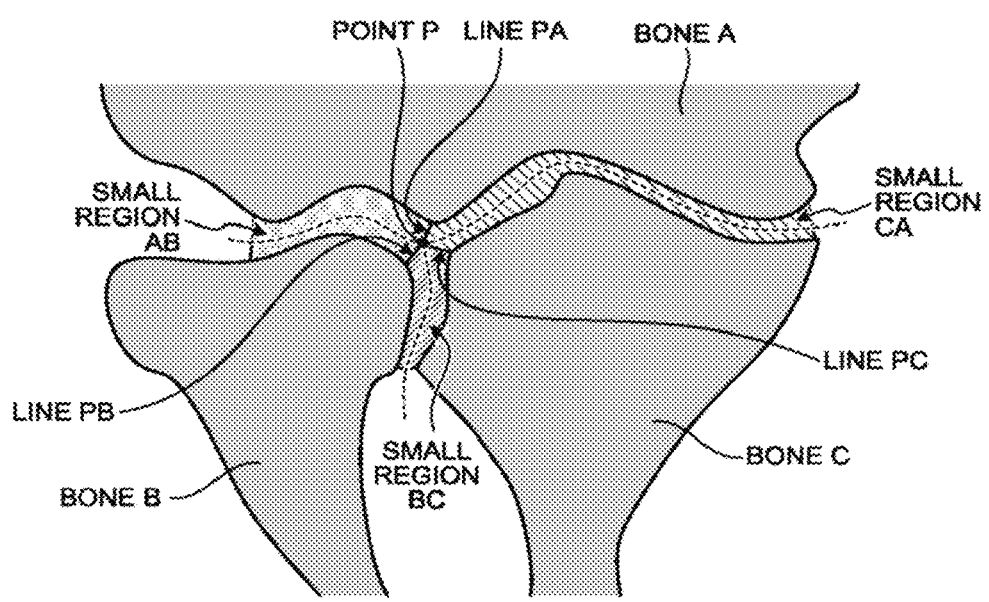
FIG. 6 is an illustration for explaining processing that a divide function according to the first embodiment performs.

FIG. 6 is an illustration for explaining processing that a divide function 372 according to the first embodiment performs. FIG. 6 illustrates a case in which the joint space region detected in FIG. 5 is divided into three small regions. While FIG. 6 explains a case in which processing is executed on X-ray CT image data in a certain frame, the same processing can be similarly executed on 4DCT image data. In connection with FIG. 6, the processing that is performed on a certain section in X-ray CT image data is described.

As illustrated in FIG. 6, the divide function 372 divides the joint space region, which is a region present between the bone A, the bone B, and the bone C, into a small region AB between the bone A and the bone B, a small region BC between the bone B and a small region CA between the bone C and the bone A. When the processing is performed on a joint formed between three or more bones, there is a branch point from which lines each equally distant from two opposed bones emerge. In the example illustrated in FIG. 6, the point P is located at a branching point from which the line between the bone A and the bone B, the line between the bone B and the bone C, and the line between the bone C and the bone A emerge. In this case, the divide function 372 divides the joint space region with shortest lines from the branching point (the point P) to the regions of the respective bones. Specifically, the divide function 372 divides the joint space region into the three small regions (small regions AB, BC, and CA) with the line PA that is the shortest among lines connecting the point P and the bone A, the line PB that is the shortest among lines connecting the point P and the bone B, and the line PC among lines connecting the point P and the bone C.

The divide function 372 identifies between which one of the pairs of bones a region corresponding to each of the small regions is present. For example, the divide function 372 specifies, as a pair of bones located across the small region, two opposed bones intersected by the opposite ends of any perpendicular of a line equally distant from the bones. In the example in FIG. 6, the respective opposite ends of a perpendicular of a line equally distant from the bones A and B that is contained in the small region AB intersect the bones A and B. In this case, the divide function 372 identifies the small region AB as a small region present between the bones A and B. Likewise, the respective opposite ends of a perpendicular of a line equally distant from the bones B and C that is contained in the small region BC intersects the bones B and C. In this case, the divide function 372 identifies the small region BC as a region present between the bones B and C. Likewise, the respective opposite ends of a perpendicular of a line equally distant from the bones C and A that is contained in the small region CA intersects the bones C and A. In this case, the divide function 372 specifies the small region CA as a region present between the bones C and A.

The divide function 372 thus divides a joint space region into small regions corresponding to the different pairs of opposed bones. In other words, based on the detected three or more bones and the shape of the joint space region, the divide function 372 divides the joint space region into a plurality of small regions corresponding to different pairs of opposed bones of the three or more bones. The above description of the detection function 371 is merely an example and is not limiting. The point P illustrated in FIG. 6 is a "line" in three-dimensional data. All of the line PA, the line PB, and the line PC are "planes" in three-dimensional data. All of the small region AB, the small region BC, and small region CA are "three-dimensional regions" in three-dimensional data.

The output control function 373 acquires related information based on the small regions into which a joint space region has been divided that correspond to the different pairs of bones, and outputs the obtained information. For example, the output control function 373 includes a calculation function 373A that calculates values for a parameter related to joints with respect to each small region. The output control function 373 then displays the values for the parameter calculated by the calculation function 373A on the display 32. The output control function 373 is an example of an output control unit.

The calculation function 373A calculates values for a parameter related to joints with respect to each small region. For example, the calculation function 373A calculates values for a parameter on the small regions with respect to each of the small regions obtained by the dividing by the divide function 372. The calculation function 373A also calculates values for a parameter on the small regions with respect to each frame of three-dimensional medical image data captured in a time sequence. The calculation function 373A is an example of a calculation unit.

Figure 7A:
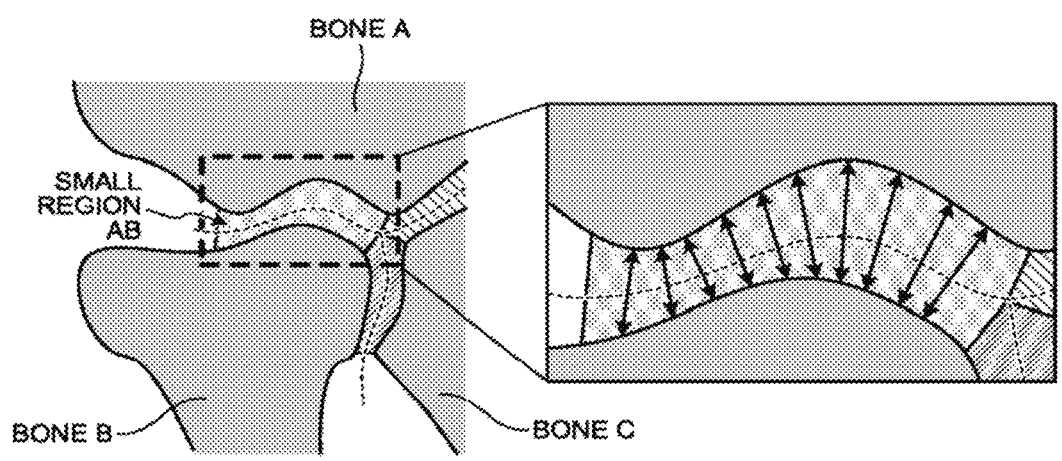
FIG. 7A and FIG. 7B are an illustration and a graph for explaining processing that a calculation function according to the first embodiment performs.
Figure 7B:
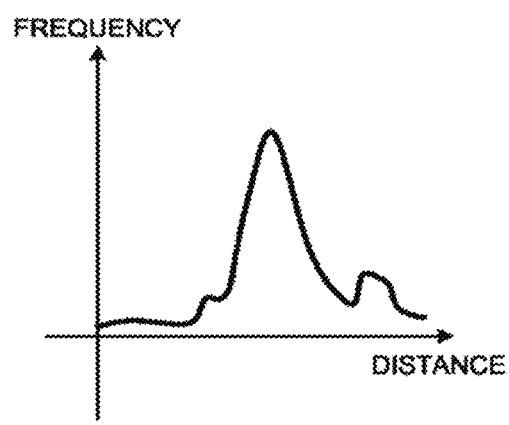

FIG. 7A and FIG. 7B are an illustration and a graph for explaining processing that the calculation function 373A according to the first embodiment performs. FIG. 7A illustrates a case when distances (space widths) between the bones are measured for the small region AB obtained by the dividing as illustrated in FIG. 6. FIG. 7B illustrates a case when a statistic (the mode) for the distances between the bones calculated as illustrated in FIG. 7A. In FIG. 7B, the horizontal axis corresponds to the distances between the bone, and the vertical axis corresponds to frequencies.

As illustrated in FIG. 7A, for example, the calculation function 373A measures, as the parameter, distances (space widths) between the bones in the small region AB. For example, the calculation function 373A measures distances to the bone A and to the bone B from a line equally distant from the bones A and B, that is, the lengths of normal vectors (arrows in the enlarged illustration in FIG. 7A that point opposite directions) of the line that start from the line and end at the bones A and at the bone B. As illustrated in FIG. 7B, the calculation function 373A generates a frequency distribution graph of the measured distances (distance histogram). The calculation function 373A calculates the mode of the distances between the bones from the distance histogram.

The calculation function 373A compares values for the parameter between the small regions. For example, the calculation function 373A calculates ratios of the values for the parameter between the plurality of small regions. Specifically, the calculation function 373A calculates ratios between the mode of the distances for the small region A, the mode of the distances for the small region BC, and the mode of the distances for the small region CA. As a result, the calculation function 373A outputs ratios such as "small region AB:small region BC:small region CA=1.0:1.2:0.9".

The calculation function 373A thus calculates a value for a parameter related to joints with respect to each small region. Furthermore, the calculation function 373A compares the calculated values for the parameter between these small regions and outputs the comparison result. The above description of the calculation function 373A is merely an example and is not limiting. For example, as the parameter for which values are calculated, any conventional parameter that is measurable in a three-dimensional region may be used. Examples of a parameter for which the calculation function 373A can calculate values include various parameters such as the volume of each small region, the maximum value of the distances, the minimum value of the distances, and the position of the centroid (coordinates).

The output control function 373 then displays the values for the parameter calculated by the calculation function 373A on the display 32. For example, on the display 32, the output control function 373 displays a value for a parameter on one joint, and a value for the parameter on another joint to be compared with the foregoing joint. For example, the output control function 373 also displays rendering images of the small regions on the display 32.

Figure 8A:
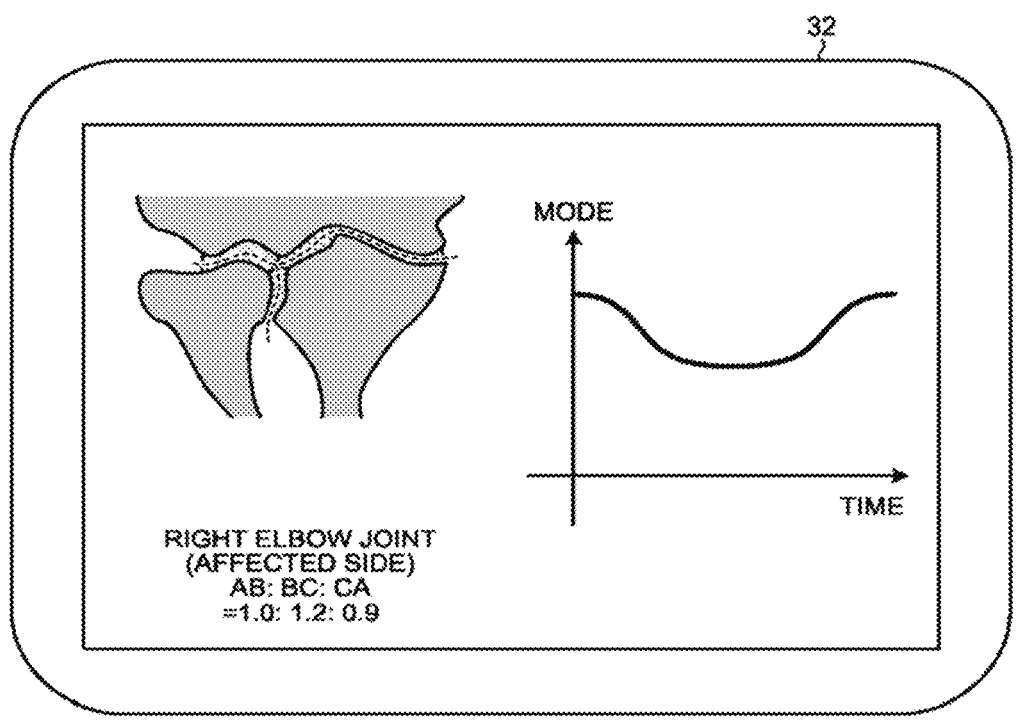
FIG. 8A and FIG. 8B are illustrations for explaining processing that an output control function according to the first embodiment performs.
Figure 8B:
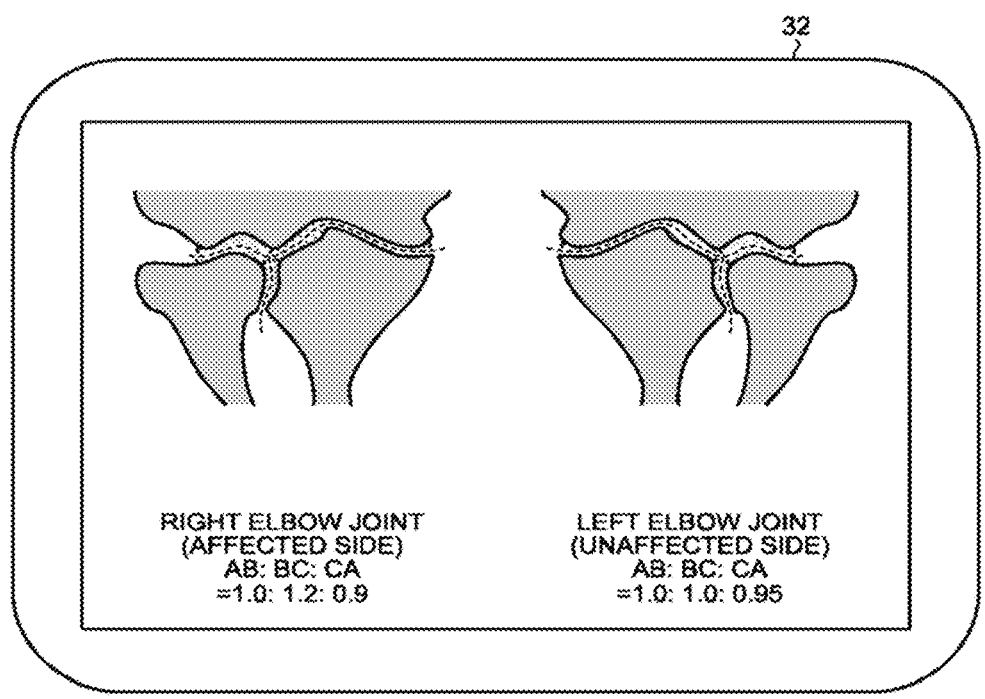

FIG. 8A and FIG. 8B are illustrations for explaining processing in the output control function 373 according to the first embodiment. FIG. 8A and FIG. 8B illustrate examples of a display screen to be displayed on the display 32.

As illustrated in the upper left part of FIG. 8A, for example, the output control function 373 displays a display image for displaying a plurality of small regions obtained by the dividing. On this display image, the regions of bones forming a joint therebetween and the small regions in a joint space between these bones are depicted. While a case of displaying a display image (the image illustrated in FIG. 6) based on a binarized image is illustrated here, this is not a limiting example. An image of any section in X-ray CT image data before binarization, or image data having the regions of the respective bones surface-rendered may be displayed. Image data having the joint space region surface-rendered may be displayed. In a surface-rendered image of the joint space region, the position at which opposed bones make contact with each other is observed as a hole in the rendered image, for example. In addition, the display image may be displayed as a still image or may be displayed as a moving image.

In the joint space region on the display image, differences between value for a parameter can be visually presented in a manner such that luminance levels according to values for a parameter (statistic) on the small regions (or colors adapted to a color lookup table) are assigned to the respective small regions. Furthermore, a threshold may be set on the parameter so that an alert (in the form of highlighting or sound) can be output if a value is higher (or lower) than a certain value.

As illustrated in the right part in FIG. 8A, the output control function 373 displays a graph representing time-sequential changes of the mode of the distances. In this graph, the horizontal axis corresponds to time, and the vertical axis corresponds to the mode of the distances. While displaying time-sequential changes of the mode of the distances is illustrated here, this is not a limiting example. The output control function 373 can display temporal changes of any desired parameter. The output control function 373 may display values for a parameter at any point in time, instead of time-sequential changes thereof. For example, the output control function 373 may display the distance histogram illustrated in FIG. 7B on the display 32, or may display numerical information instead of a graph. When the graph in FIG. 7B is displayed, the coordinate system thereof can be changed into a three-dimensional one with an axis corresponding to time added thereto, so that time-sequential changes can be displayed. Alternatively, the time-sequential changes may be represented with the graph of FIG. 7B displayed as moving images that move over time.

As illustrated in the lower left part of FIG. 8A, the output control function 373 displays ratios between the plurality of small regions can the display 32. For example, when the calculation function 373A has calculated the ratios of the modes of distances as "small region AB:small region BC:small region CA=1.0:1.2:0.9", the output control function 373 displays the numerical information, "AB:BC:CA=1.0:1.2:0.9", on the display 32.

As illustrated in FIG. 8B, the output control function 373 displays information on a joint in the affected side and information on a joint in the unaffected side on the display 32. For example, the output control function 373 concurrently displays an image of a right elbow joint as a joint in the affected side of a patient (the subject P) (the upper left part of FIG. 8B) and an image of a left elbow joint as a joint in the unaffected side of the patient (the upper right part of FIG. 8B). The output control function 373 also displays ratios between a plurality of small regions in the affected side and ratios between those in the unaffected side separately at the same time. Thus, an image and values (ratios) of a joint in the affected side of a patient can be compared with of a joint in the unaffected side thereof. While a case of comparing a joint in the affected side of a patient with a joint in the unaffected side thereof is illustrated here, this is not a limiting example. For example, the output control function 373 compares pre-therapeutic and post-therapeutic states of the same joint of a patient with each other, or may compare a joint of a patient with a movement model of a standard joint.

The output control function 373 thus displays various processing results on the display 32. In other words, the output control function 373 obtains information on each of the small regions based on the small regions into which a joint space region has been divided that correspond to the different pairs of bones, and outputs the obtained information. The above description of the output control function 373 is merely an example and is not limiting.

Figure 9:
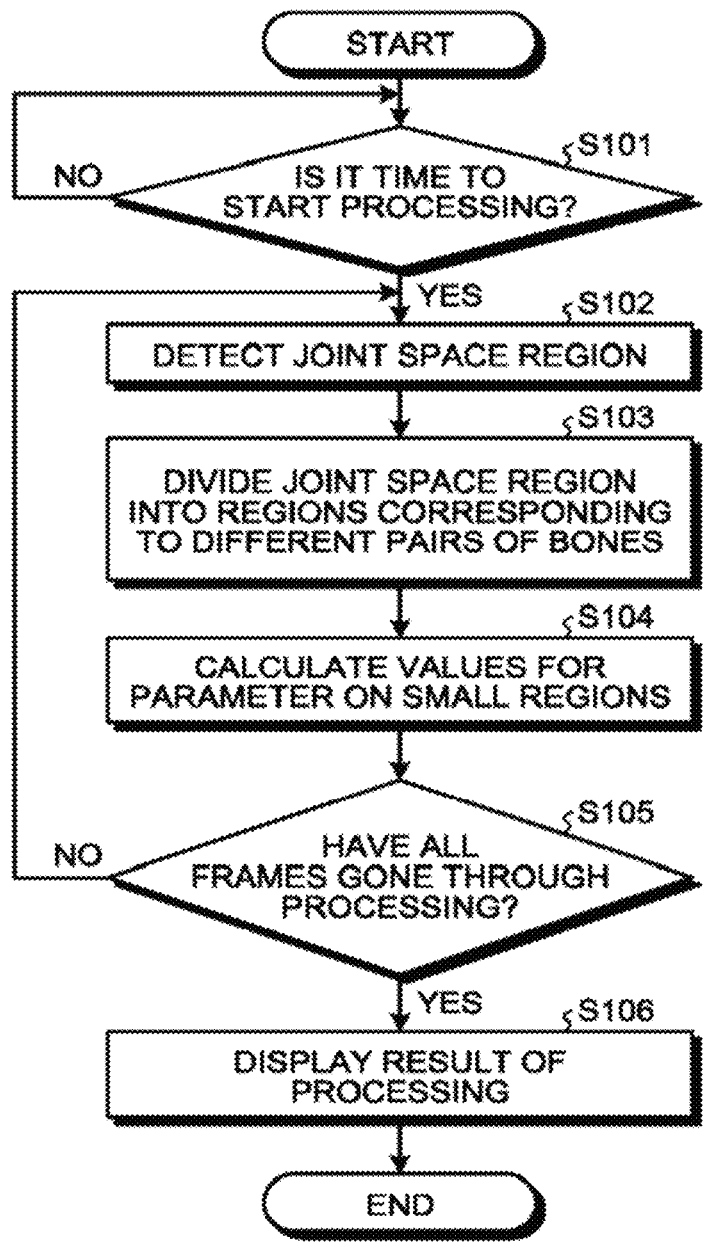
FIG. 9 is a flowchart illustrating the procedure of processing that an X-ray CT apparatus according to the first embodiment performs.

FIG. 9 is a flowchart illustrating the procedure of processing in an X-ray CT apparatus 1 according to the first embodiment. The processing procedure illustrated in FIG. 9 is started with an operator inputting an instruction to start quantitative evaluation on a joint space.

As illustrated in FIG. 9, the processing circuitry 37 determines at Step S101 whether quantitative evaluation on a joint space has been started. For example, if the operator has input an instruction to start quantitative evaluation on a joint space, the processing circuitry 37 determines that it is the time to start processing, and starts processing at Step S102 and the subsequent steps. If the determination at Step S101 is negative, the processing circuitry 37 goes standby without starting quantitative evaluation on a joint space.

If the determination at Step S101 is affirmative, the detection function 371 detects a joint space region at Step S102. For example, the detection function 371 detects, as the joint space region, a region that includes a plane equally distant from each two opposed bones among a plurality of bones and that includes perpendiculars of the plane with the opposite ends of each of the perpendiculars intersecting these two opposed bones.

At Step S103, the divide function 372 divides the joint space region into regions corresponding to different pairs of bones. For example, the divide function 372 divides a joint space region while taking, as each of the pairs of bones, two opposed bones that are intersected by the opposite ends of any perpendicular of a line equally distant from these bones.

At Step S104, the calculation function 373A calculates values for a parameter on small regions. For example, the calculation function 373A calculates values for a parameter on small regions with respect to the small regions.

At Step S105, the processing circuitry 37 determines whether all frames have gone through the processing. For example, upon determining that the processing has been executed on all frames contained in 4DCT image data, the processing circuitry 37 executes processing at Step S106. If the determination at Step S105 is negative, the processing circuitry 37 repeatedly executes processing at Step S102 to Step S104 until the completion of X-ray CT image data in all frames contained in 4DCT image data.

If the determination at Step S105 is affirmative, the output control function 373 displays the result of the processing at Step S106. For example, on the display 32, the output control function 373 displays information obtained based on small regions into which the joint space region has been divided into regions corresponding to different pairs of bones.

The processing procedure of FIG. 9 is merely an example and is not limiting. For example, the above processing procedure need not necessarily be executed in the above-described order. For example, image data of small regions may be displayed on the display 32 each time processing for dividing X-ray CT image data in one frame into the small regions is executed.

As described above, in the X-ray CT apparatus 1 according to the first embodiment, the X-ray tube 12a emits X-rays to a region of a subject that has a joint formed between three or more bones. The detector 13 then detects X-rays that have passed through the region of the subject. The image reconstruction circuitry 36 reconstructs three-dimensional medical image data based on detection data of the X-rays detected by the detector 13. From three-dimensional medical image data captured for images of a joint formed between three or more bones, the detection function 371 detects a joint space region that corresponds to a joint space of the joint. The divide function 372 then divides the joint space region into regions corresponding to different pairs of opposed bones of those three or more bones. The output control function 373 then obtains related information based on small regions into which the joint space region has been divided that correspond to the different pairs of opposed bones, and outputs the obtained information. Thus, the X-ray CT apparatus 1 according to the first embodiment enables accurate and simplified quantitative evaluation on a joint space.

For example, when an operator manually extracts a joint space region, such manual extraction is time-consuming. For this reason, performing quantitative evaluation on all frames (time phases) of 4DCT image data is not realistic. In addition, such manual extraction tends to incur variations in the extracted joint space region and thus makes it difficult to achieve reproducibility. In contrast, the X-ray CT apparatus 1 according to the first embodiment automatically extracts a joint space region. The X-ray CT apparatus 1 therefore enables quantitative evaluation on joint spaces using 4DCT image data and enables obtaining evaluation results with high reproducibility.

When a joint space region is automatically extracted using a dedicated computer program, joints selectable as those that can be evaluated are limited for such reasons as that the dedicated computer program only allows evaluation on specific joints. In addition, some dedicated computer programs are not applicable to a joint formed between a plurality of bones. In contrast, the X-ray CT apparatus 1 according to the first embodiment automatically extracts a joint space region by identifying the positional relationships between bones in X-ray CT image data through biological structural analysis. The X-ray CT apparatus 1 is therefore capable of automatically extracting a joint space region without limitation of joints to be evaluated and without limitation of the number of bones between which a joint is formed.

Furthermore, a dedicated computer program has a risk of being unable to correctly extract a joint space region because of the influence of artifacts. In contrast, the X-ray CT apparatus 1 according to the first embodiment is capable of processing 4DCT image data, which represent moving images, and therefore can reduce the influence of artifacts by referring to image data of time phases less susceptible to artifacts.

When quantitative measurement using X-ray projection image data is performed from extracted and emphasized edge points in a limited region such as a knee joint or a hip joint, image data on which the processing is performed is limited to two-dimensional projection data, the same processing cannot be performed on three-dimensional image data. For this reason, the X-ray CT apparatus 1 according to the first embodiment detects the region of a bone by using X-ray CT image data obtained based on CT values that are commonly applicable. The X-ray CT apparatus 1 can then identify a joint space region by analyzing feature scores of a three-dimensional data distribution of the detected region of a bone.

The X-ray CT apparatus 1 according to the first embodiment is applicable to 4DCT image data captured while a subject is moving a joint. Therefore, temporal changes for a relatively short period of time while the joint is being moved is calculated and displayed as quantitative information. For example, the X-ray CT apparatus 1 is capable of displaying values for any measurable parameters such as a parameter indicating decrease of cartilage, the volume of a joint space, temporal changes of the maximum value and the minimum value of the distances, and the centroid and the distribution of a distance histogram.

Moreover, from three-dimensional medical image data captured for images of a joint formed between a plurality of bones, the X-ray CT apparatus 1 according to the first embodiment detects, as a joint space region, a region between two opposed ones of these bones that includes perpendiculars of a plane equally distant from the two opposed bones with the opposite ends of each of the perpendiculars intersecting the two respective bones, for example. The X-ray CT apparatus 1 then obtains related information based on the region and outputs the obtained information. Thus, the X-ray CT apparatus 1 enables an operator to detect a region corresponding to a joint space with simple operations to analyze the joint space.

Other Embodiments

Various embodiments other than the above-described embodiment may be implemented.

Medical Image Processing Apparatus

For example, while the above embodiment has been described as a case in which the respective processing functions that the detection function 371, the divide function 372, and the output control function 373, which are components of the processing circuitry 37, execute are executed in the X-ray CT apparatus 1, other embodiments are not limited to this case. For example, the above processing functions may be executed in a medical image processing apparatus such as a work station.

That is, the medical image processing apparatus includes processing circuitry that is the same as the processing circuitry 37. This processing circuitry executes the same function as the detection function 371, the same function as the divide function 372, and the same function as the output control function 373. That is, in the medical image processing apparatus, the same function as the detection function 371 detects a joint space region from three-dimensional medical image data captured for images of a joint formed between three or more bones, the joint space region corresponding to a joint space of the joint. The same function as the divide function 372 then divides the joint space region into regions corresponding to different pairs of opposed bones of those three or more bones. The same function as the output control function 373 then obtains related information based on small regions into which the joint space region has been divided that correspond to the different pairs of opposed bones, and outputs the obtained information. Thus, the medical image processing apparatus enables accurate and simplified quantitative evaluation on a joint space.

Calculation of Contact Area Between Small Region and Bone

For example, the contact area between a small region and a bone may be calculated as a parameter related to joints. That is, the calculation function 373A can calculate, as the parameter related to joints, the contact area of the interface between each small region and at least one of the two bones between which the small region is formed.

Figure 10:
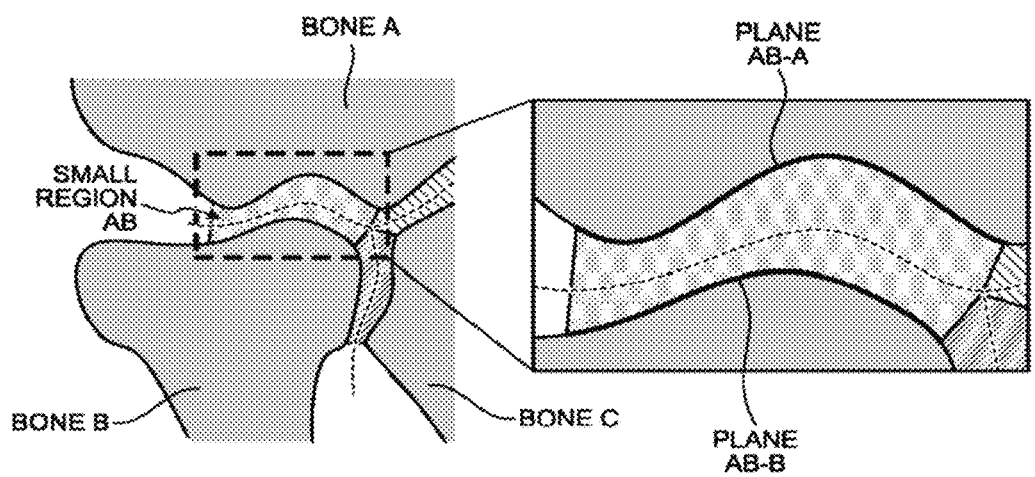
FIG. 10 is an illustration for explaining processing that a calculation function according to another embodiment performs.

FIG. 10 is an illustration, for explaining processing that a calculation function 373A according to another embodiment performs. FIG. 10 illustrates a case in which the areas of the plane AB-A and the areas of the plane AB-B are calculated. Here, the plane AB-A corresponds to the interface between the small region AB and the bone A, which are illustrated in FIG. 6. The plane AB-B corresponds to the interface between the small region AB and the bone B, which are illustrated in FIG. 6.

As illustrated in FIG. 10, the calculation function 373A calculates the area of the plane AB-A for example. Specifically, the calculation function 373A specifies the coordinates of the interface between the small region AB and the bone A, based on the coordinates of the contour of the small region AB and the coordinates of the contour of the bone A in volume data. The calculation function 373A then calculates the area of the interface thus specified. The calculation function 373A thus calculates the area of the plane AB-A. The calculation function 373A can perform similar processing to calculate the areas of the plane AB-B, the plane BC-B (the interface between the small region BC and the bone B), the plane BC-C (the interface between the small region BC and the bone C), and so on.

Thus, symptoms at the joint can be analyzed in detail. For example, it is difficult to determine whether a reduction in volume of the small region AB indicates that the distance between the bone A and the bone B has become smaller or that the small region AB has become smaller because either or both of the bone A and the bone B have been worn away. In such a case, if the area of the plane AB-A is found to have become smaller, it suggests that the bone A has been worn out. If the area of the plane AB-B is found to have become smaller, it suggests that the bone B has been worn out. Otherwise, if the areas of the plane AB-A and the plane AB-B have been both unchanged, it suggests that the distance between the bone A and the bone B has become smaller. Detailed analysis on the small region AB contained in the joint is thus made possible.

The example in FIG. 10 is not limiting. For example, the calculation function 373A may calculate, as the area of the small region AB, the sum of the areas of the plane AB-A and the plane AB-B. The calculation function 373A may calculate, as the area of the small region AB, the sum of the areas of the plane AB-A and the plane AB-B. The above-described area calculation method is merely an example, and any other conventional calculation method (image analysis method) may be applied to the calculation.

Display of Comparison Using Graphs

The output control function 373 can display comparison using graphs.

Figure 11:
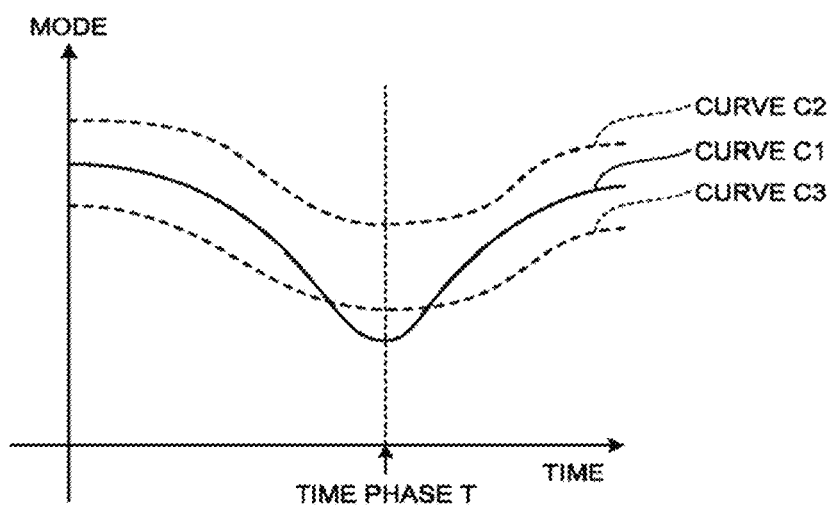
FIG. 11 is a graph for explaining processing that an output control function according to still another embodiment performs.

FIG. 11 is a graph for explaining processing that an output control function 373 according to still another embodiment performs. FIG. 11 illustrates a graph (the curve C1) representing time-sequential changes of the mode of the distances in a right elbow joint of a patient and graphs (the curve C2 and the curve C3) each representing the time-sequential changes of the mode of distances in a standard right elbow joint (standard data). The curve C2 represents the upper limit of the standard data, and the curve C3 represents the lower limit of the standard data. The standard data is obtained, for example, based on the 95% confidence interval from the distribution of the modes of the distances in right elbow joints of normal subjects. In FIG. 11, the horizontal axis corresponds to time, and the vertical axis corresponds to the modes.

As illustrated in FIG. 11, on the display 32, the output control function 373 displays a graph (the curve C1) representing time-sequential changes of a parameter, and graphs to be compared representing time-sequential changes (the curve C2 and the curve C3) of the parameter for subjects to be compared. Specifically, the output control function 373 displays the curve C1 based on values for the parameter that have been measured from image data of the right elbow joint of the patient. The output control function 373 also displays the curve C2 and the curve C3 based on the standard data.

On the display 32, the output control function 373 can also display a medical image related to a joint, based on comparison between the graph and each of the graphs to be compared. For example, the output control function 373 automatically displays an image of a joint at a time phase at which the curve C1 has a value that deviates the most from the standard data. In the example illustrated in FIG. 11, the output control function 373 identifies the time phase T as a time phase at which the curve C1 has a value that deviates the most from the standard data. On the display 32, the output control function 373 then displays a medical image of the right elbow joint at the identified time phase T. Thus, the operator is enabled to easily compare values for the parameter for the joint of the patient with values for the parameter for the subjects to be compared.

The example illustrated in FIG. 11 is merely an example and is not limiting. For example, while FIG. 11 illustrates a case of comparison with standard data, embodiments are not limited thereto. For example, the operator is also enabled to compare an affected side and an unaffected side provided that a site of interest is included in sites that are located in the left and right sides and have mirror images of each other. Specifically, when the right elbow joint is affected (the affected side), the right elbow joint may be compared with the left elbow joint of the same patient. The vertical axis and the horizontal axis of the graphs can be set to any desired parameters.

While FIG. 11 illustrates a case in which an image at a time phase at which the deviation from the standard data is the largest is automatically displayed, embodiments are not limited to this case. For example, the output control function 373 can display a medical image at a time phase specified by an operator. In a specific example, when the operator specifies the position of the time phase T on the graph of FIG. 11, the output control function 373 displays a medical image of the right elbow joint of the patient at the time phase T on the display 32.

While FIG. 11 illustrates a condition example that involves the deviation from the standard data at the time phase T, embodiments are not limited to such an example. For example, the display of comparison is beneficial also in a condition example that involves a graph that is lower (or higher) as a whole than the standard data.

The components of the illustrated apparatuses are functionally conceptual, and need not be physically configured as illustrated in the drawings. That is, the specific forms of distribution and integration of the apparatuses are not limited to those illustrated in the drawings, and all or some of the apparatuses can be configured in a functionally or physically distributed or integrated manner in any desired units depending on various types of loads or use conditions. Furthermore, all or any part of the processing functions performed in the apparatuses can be implemented in the form of a CPU and a computer program to be analyzed and executed by the CPU, or can be implemented in the form of hardware using a wired logic.

In the processing described in the above embodiments, all or part of the processing described as processing to be automatically performed may be performed manually, and all or part of the processing described as processing to be manually performed may be performed automatically using a known method. In addition, the processing procedures, the control, procedures, the specific names, and the information, including various data and parameters, that have been provided in the above description and the drawings can be changed as desired, unless otherwise stated.

The medical image processing method described in the above embodiments can be implemented upon execution, on a computer such as a personal computer or a workstation, of a medical image processing program provided in advance. This medical image processing program can be distributed through a network such as the Internet. This medical image processing method can also be recorded on a computerreadable recording medium such as a hard disk, a flexible disk (FD), a compact disc read-only memory (CD-ROM), a magneto-optical (MO) dish, or a digital versatile disc (DVD) and executed by being read out from the recording medium by a computer.

At least one of the embodiments described above enables accurate and simplified quantitative evaluation on a joint space.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
 processing circuitry configured to:
  detect three or more bones and a joint space region from three-dimensional medical image data captured for images of a joint formed between the three or more bones, the joint space region corresponding to a joint space of the joint,
  divide the joint space region into a plurality of small regions corresponding to each of different pairs of opposed bones between which each of the small regions is present, the different pairs of opposed bones being chosen from the three or more bones,
  assign pair information indicating the different pairs of opposed bones between which each of the small regions is present to the joint space region,
  obtain information on each of the small regions based on the small regions into which the joint space region has been divided that correspond to the different pairs of bones, the obtained information including the pair information, and
  output the obtained information, wherein
 the processing circuitry is further configured to detect temporal change of the joint space region with respect to multiple frames of the three-dimensional medical image data captured in a time sequence in a single main imaging, and obtain the information on each of the small regions with respect to the multiple frames.

2. The medical image processing apparatus according to claim 1, wherein the processing circuitry detects, as the joint space region, a region that includes a plane equally distant from two opposed bones of the three or more bones and that includes perpendiculars of the plane with opposite ends of each of the perpendiculars intersecting the two opposed bones.

3. The medical image processing apparatus according to claim 2, wherein the processing circuitry divides the joint space region by setting, as each of the pairs of bones, two bones intersected by the opposite ends of each of the perpendiculars.

4. The medical image processing apparatus according to claim 1, wherein the processing circuitry
 divides the joint space region with respect to the multiple frames in the three-dimensional medical image data.

5. The medical image processing apparatus according to claim 1, wherein the processing circuitry calculates a value for a parameter related to joints with respect to each of the small regions and displays the calculated value for the parameter on a display.

6. The medical image processing apparatus according to claim 5, wherein the processing circuitry calculates, as the parameter related to joints, a contact area of an interface between each of the small regions and at least one of the two bones between which the small region is formed.

7. The medical image processing apparatus according to claim 5, wherein the processing circuitry
 compares the values for the parameter between the small regions and
 displays a result of the comparison on the display.

8. The medical image processing apparatus according to claim 5, wherein, on the display, the processing circuitry displays a value for the parameter related to the joint, and a comparable value for the parameter on another joint to be compared with the foregoing joint.

9. The medical image processing apparatus according to claim 8, wherein, on the display, the processing circuitry displays a graph representing temporal changes in the values for the parameter with respect to multiple frames of the three-dimensional medical image data captured in a time sequence, and another graph, to be compared with the foregoing graph, representing temporal changes in the comparable values for the parameter with respect to the multiple frames of the three-dimensional medical image data captured in a time sequence.

10. The medical image processing apparatus according to claim 9, wherein, on the display, the processing circuitry displays a medical image related to the joint, based on comparison between the graph and the graphs to be compared therewith.

11. The medical image processing apparatus according to claim 1, wherein, on the display, the processing circuitry displays a rendered image of each of the small regions.

12. An X-ray CT apparatus comprising:
 an X-ray tube configured to emit X-rays to a region of a subject that has a joint formed between three or more bones;
 a detector configured to detect X-rays that have passed through the region of the subject;
 image reconstruction circuitry configured to reconstruct three-dimensional medical image data based on detection data of the X-rays detected by the detector; and
 processing circuitry configured to
  detect the three or more bones and a joint space region from the three-dimensional medical image data, the joint space region corresponding to a joint space of the joint,
  divide the joint space region into a plurality of small regions corresponding to each of different pairs of opposed bones between which each of the small regions is present, the different pairs of opposed bones being chosen from the three or more bones,
  assign pair information indicating the different pairs of opposed bones between which each of the small regions is present to the joint space region,
  obtain information on each of the small regions based on the small regions into which the joint space region has been divided that correspond to the different pairs of bones, the obtained information including the pair information, and
  output the obtained information, wherein
 the processing circuitry is further configured to detect temporal change of the joint space region with respect to multiple frames of the three-dimensional medical image data captured in a time sequence in a single main imaging, and obtain the information on each of the small regions with respect to the multiple frames.

13. The medical image processing apparatus according to claim 1, wherein the multiple frames of the three-dimensional medical image data is captured while the joint is moved.

14. The X-ray CT apparatus according to claim 12, wherein the multiple frames of the three-dimensional medical image data is captured while the joint is moved.

* * * * *